United States Patent
Thornton

[19]

[11] Patent Number: 5,807,100

[45] Date of Patent: Sep. 15, 1998

[54] DENTAL DEVICE HAVING AN IMPROVED DEFORMABLE MATERIAL AND METHOD FOR FORMING SAME

[76] Inventor: W. Keith Thornton, 5524 Edlen, Dallas, Tex. 75220

[21] Appl. No.: 653,285

[22] Filed: May 24, 1996

[51] Int. Cl.[6] ..................................... A61C 9/00
[52] U.S. Cl. .......................... 433/48; 433/214; 128/862
[58] Field of Search .................. 433/6, 48, 71, 433/214; 128/857, 858, 862

[56] References Cited

U.S. PATENT DOCUMENTS

| | | | |
|---|---|---|---|
| 2,505,028 | 4/1950 | Boeger | 433/90 |
| 3,064,354 | 11/1962 | Pos | 32/19 |
| 3,690,004 | 9/1972 | Frush | 32/17 |
| 3,882,601 | 5/1975 | Jahn | 32/17 |
| 4,227,877 | 10/1980 | Tureaud et al. | 433/37 |
| 4,530,662 | 7/1985 | Andersson et al. | 433/37 |
| 4,686,188 | 5/1987 | Wolfenson et al. | 433/37 |
| 4,784,123 | 11/1988 | Robeson | 128/90 |
| 4,892,478 | 1/1990 | Tateosian | 433/6 |
| 5,011,407 | 4/1991 | Pelerin | 433/48 |
| 5,026,278 | 6/1991 | Oxman et al. | 433/41 |
| 5,040,976 | 8/1991 | Ubel, III et al. | 433/41 |
| 5,055,039 | 10/1991 | Abbatte et al. | 433/24 |
| 5,064,371 | 11/1991 | Smeltzer | 433/37 |
| 5,066,231 | 11/1991 | Oxman et al. | 433/48 |
| 5,112,225 | 5/1992 | Diesso | 433/48 |
| 5,190,457 | 3/1993 | Schreinemakers | 433/214 |
| 5,213,498 | 5/1993 | Pelerin | 433/37 |
| 5,320,533 | 6/1994 | Lee | 433/215 |
| 5,370,533 | 12/1994 | Bushnell | 433/36 |
| 5,415,544 | 5/1995 | Oxman et al. | 433/214 |
| 5,503,552 | 4/1996 | Diesso | 433/37 |
| 5,551,872 | 9/1996 | Mena | 433/37 |
| 5,562,449 | 10/1996 | Jacobs et al. | 433/48 |
| 5,582,517 | 12/1996 | Adell | 433/6 |

FOREIGN PATENT DOCUMENTS

WO9112777  9/1991  WIPO .

OTHER PUBLICATIONS

PCT International Search for PCT application PCT/US97/087008.

*Primary Examiner*—Cary E. O'Connor
*Attorney, Agent, or Firm*—Baker & Botts, L.L.P.

[57] ABSTRACT

A dental device (10, 11) includes an arch (12, 14) adapted to receive one or more of a user's teeth (16). A deformable material (20, 32) is coupled to the arch (12, 14) and includes an aliphatic polyester. The aliphatic polyester may be a polycaprolactone polymer and may have the formula:

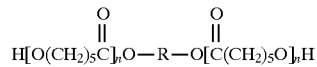

where R is an aliphatic hydrocarbon.

22 Claims, 2 Drawing Sheets

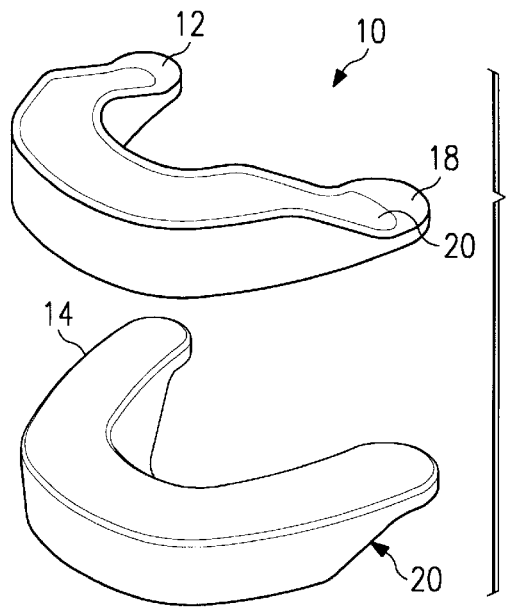
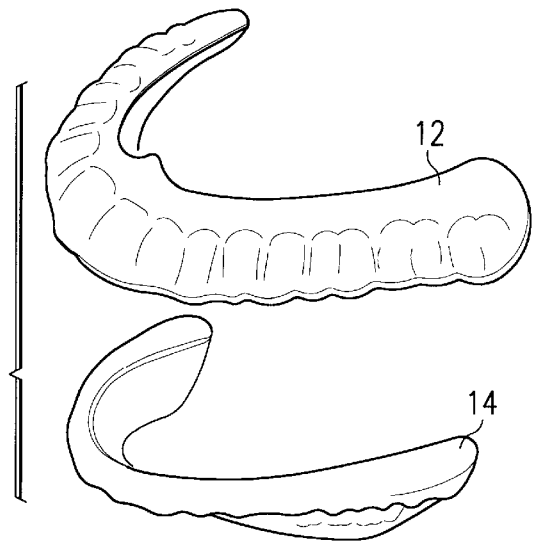
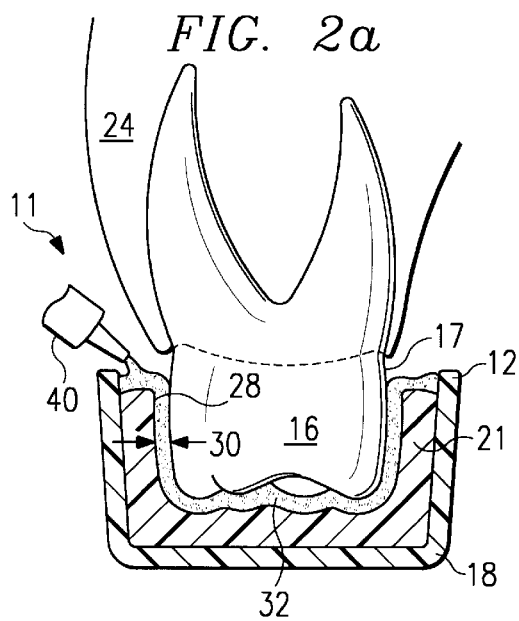
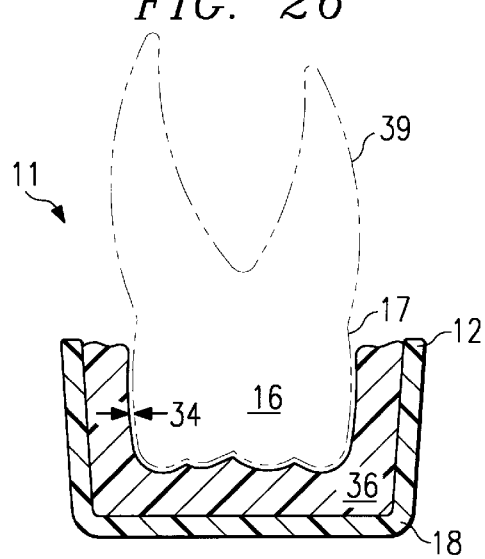

DENTAL DEVICE HAVING AN IMPROVED DEFORMABLE MATERIAL AND METHOD FOR FORMING SAME

This Application is related to copending application Ser. No. 08/695,862, filed Aug. 5, 1996 by W. Keith Thornton for a System and Method for Customizing a Dental Device Using an Improved Deformable Material. This Application is also related to copending application Ser. No. 08/621,133, filed Mar. 21, 1996 by W. Keith Thornton for a Relined Dental Device and Method.

TECHNICAL FIELD OF THE INVENTION

This invention relates generally to dental devices, and more particularly to a dental device having an improved deformable material and a method for forming the same.

Background of the Invention

Many dental devices include a deformable material for forming a mold of some or all of a user's teeth. It is often desirable to form a mold that properly fits the user's teeth to improve the performance of the associated dental device. Dental devices that do not properly fit the user's teeth may not adequately serve the purposes for which the devices are constructed.

As dental devices become increasingly complex to satisfy a variety of treatment, comfort, safety, and other requirements, users or clinical professionals may wish to form a mold that more optimally fits the user's teeth. A known technique for forming a mold of a user's teeth includes inserting a heat-deformable mouthpiece into the user's mouth, pressing the user's teeth into the mouthpiece, and removing the mouthpiece from the user's mouth after the mouthpiece has cooled. Such techniques may not provide a proper fit, however, due to the tendency of many deformable materials to contract during cooling, thereby expanding the impressions made by the user's teeth. In addition, this technique must often be repeated numerous times before even a marginally adequate fit can be achieved.

Deformable materials used in connection with such techniques may also cool more quickly and display less thermoplasticity at certain temperatures than the user or clinical professional might desire, thereby limiting the time in which the user or clinical professional may manipulate the deformable material to form a mold of the user's teeth. Furthermore, mouthpieces fitted using such techniques may be less safe for the user due to the increased tendency of the user's teeth to move with respect to a mouthpiece that does not properly fit the user's teeth. Moreover, many deformable mouthpiece materials may display insufficient dimensional stability during cooling, bonding properties, hardness, or biocompatibility to function properly in a variety of contexts.

SUMMARY OF THE INVENTION

In accordance with the present invention, the disadvantages and problems associated with dental devices and methods that include a deformable material have been substantially reduced or eliminated.

In accordance with one embodiment of the present invention, a dental device includes an arch adapted to receive one or more of a user's teeth. A deformable material is coupled to the arch and includes an aliphatic polyester. In a more particular embodiment, the aliphatic polyester is a polycaprolactone polymer that has the formula:

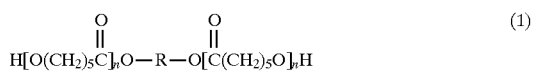

where R is an aliphatic hydrocarbon.

Important technical advantages of the present invention include providing a dental device and method that include an improved deformable material to more optimally fits the user's teeth. Improved fit may be important in connection with dental devices designed to reduce or eliminate trauma injuries or breathing problems such as sleep apnea. The present invention provides desirable hardness, biocompatibility, dimensional stability during cooling, thermoplasticity, and bonding properties for a variety of contexts. Other technical advantages are readily apparent to one skilled in the art from the following figures, descriptions, and claims.

BRIEF DESCRIPTION OF THE DRAWINGS

For a more complete understanding of the present invention and for further features and advantages thereof, reference is now made to the following description taken in conjunction with the accompanying drawings, in which:

FIGS. 1a and 1b illustrate dental devices having an improved deformable material;

FIGS. 2a and 2b illustrate a method for relining a dental device using an improved deformable material.

DETAILED DESCRIPTION OF THE INVENTION

Figure 3A:
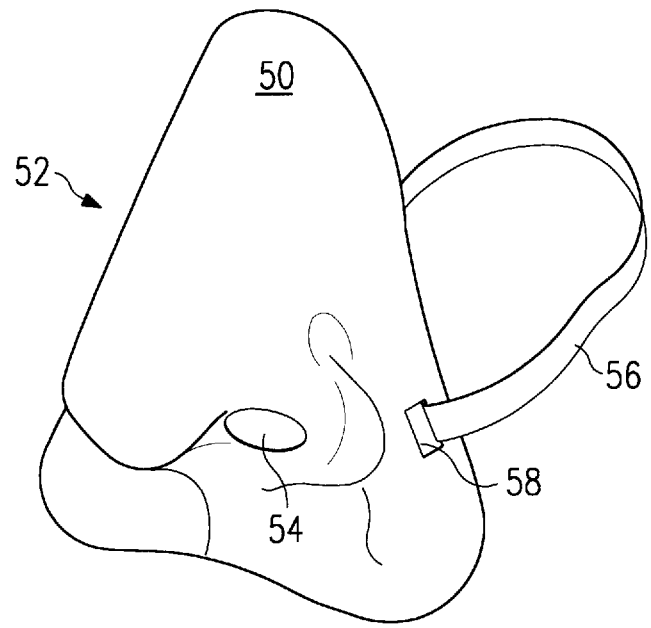
FIGS. 3a and 3b illustrate masks having an improved deformable material.

FIG. 1a illustrates a dental device 10 that includes an upper arch 12 adapted to receive one or more of a user's upper teeth and a lower arch 14 adapted to receive one or more of the user's lower teeth. When dental device 10 is in use, upper arch 12, lower arch 14, or both upper arch 12 and lower arch 14 are inserted into the user's mouth. Although device 10 may include upper arch 12, lower arch 14, or both upper arch 12 and lower arch 14, device 10 is discussed below as including only upper arch 12. It should be understood that the following discussion applies equally to a device 10 that includes lower arch 14 instead of, or in addition to, upper arch 12.

Upper arch 12 includes a tray 18 formed from any material suitable for dental uses, for example, methyl methacrylate or a polycarbonate resin thermoplastic such as that sold under the Registered Trademark Lexan. Such materials are known to those familiar with dental devices, and other suitable materials may be used to form tray 18 without departing from the intended scope of the present invention. For example, tray 18 may also be formed from one or more other thermoplastic polymers, such as one or more of the polycaprolactone polymers or other aliphatic polyesters described in U.S. Pat. Nos. 5,112,225 and 4,784,123, both of which are herein incorporated by reference, as well as in literature distributed by Union Carbide Corporation. One or more polycaprolactone polymers may be combined in some manner with one or more other polymers or other suitable materials to form a tray 18 having any number of characteristics, properties, or uses. The present invention contemplates using one or more polycaprolactone polymers or other suitable aliphatic polyesters to replace or combine with methyl methacrylate for any suitable dental application.

Tray 18 is adapted to receive a deformable material 20 in which molds of one or more of the user's upper teeth may be formed. In one embodiment, deformable material 20 includes one or more of the polycaprolactone polymers or other aliphatic polyesters discussed above. One or more of the polycaprolactone polymers may have the formula:

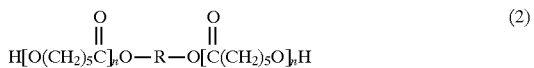
$$H[O(CH_2)_5C]_nO-R-O[C(CH_2)_5O]_nH \qquad (2)$$

where R is an aliphatic hydrocarbon and n may range from approximately 300 to approximately 650. The present invention contemplates polycaprolactone polymers having other suitable formulas.

Deformable material 20 may include any suitable polycaprolactone polymer or other aliphatic polyester, for example, and not by way of limitation, the TONE P-700, TONE P-767, or TONE P-787 polycaprolactone polymers manufactured by Union Carbide Corporation, taken singly or in any combination. A suitable light cured material, another polymer, or any other suitable material, such as a filler, coloring agent, stabilizer, antioxidant, or antimicrobial agent, may be used to replace or combine with one or more of the polycaprolactone polymers in forming a deformable material 20 having any number of characteristics, properties, or uses.

The TONE polycaprolactone polymers are described in U.S. Pat. Nos. 5,112,225 and 4,784,123, and in literature distributed by Union Carbide Corporation, as homopolymers, block copolymers, graft copolymers, or other polymers that contain epsilon-caprolactone. Polymerization may be initiated using one or more diols, for example, and not by way of limitation, ethylene glycol; diethylene glycol; neopentyl glycol; butane diol; hexane diol; or any other suitable diol. One or more of the diols may have the formula:

$$HO-R-OH \qquad (3)$$

where R is an aliphatic hydrocarbon.

In one embodiment, deformable material 20 includes approximately thirty (30) parts by volume TONE P-700 and sixty (60) parts by volume TONE P-767, together with approximately ten (10) parts by volume of one or more other polymers, depending on the application. The present invention contemplates forming an impression material such as deformable material 20 using any suitable mixture or combination of one or more polycaprolactone polymers, one or more other polymers, and one or more other suitable materials, compounds, or compositions.

Deformable material 20 may begin as one or more extruded pellets, beads, or rods of uniform, similar, or differing size, or in other suitable form. Deformable material 20 is heated in a microwave oven, in water or other non-solvent neutral liquid, or in any other suitable manner to between approximately 140 degrees Fahrenheit and approximately 180 degrees Fahrenheit to place deformable material 20 in its deformable state. Deformable material 20 may be kept in a deformable state until the pellets, beads, or rods congeal, coalesce, or otherwise combine to form a deformable mass capable of assuming a multitude of shapes and configurations. Deformable material 20 may be placed in a deformable state before, during, or after deformable material 20 is coupled to tray 18. The present invention contemplates deformable material 20 mixing, reacting, or otherwise combining with the material used to form tray 18 while deformable material 20 is in a deformable state.

Upper arch 12, including tray 18 and deformable material 20, is inserted into the user's mouth separately from or together with lower arch 14. The user bites down or otherwise presses one or more of the user's teeth into deformable material 20 in order to form a mold of one or more of the user's teeth. Deformable material 20 is then allowed to cool and harden or otherwise take a more permanent shape. These steps may be repeated as many times as necessary or desired to form a mold of one or more of the user's teeth using deformable material 20.

An important technical advantage of the present invention is that deformable material 20 may cool more slowly and may display thermoplastic properties at lower temperatures than materials such as the ethylene-vinyl acetate copolymer resin sold under the Registered Trademark Elvax. This provides the user or clinical professional with more time to properly conform deformable material 20 to the user's teeth. In addition, deformable material 20 may display increased dimensional stability during the cooling process, relative to Elvax, which may reduce or eliminate fitting problems that might otherwise develop due to the tendency of materials such as Elvax to contract during cooling, thereby expanding the impressions made by the user's teeth.

Upper arch 12 may remain inserted in the user's mouth or may be removed from the user's mouth before, during, or after deformable material 20 cools. Deformable material 20 may be formed into a mold of one or more of the user's teeth in the user's home, in the office of a clinical professional, or in any other suitable location. The present invention contemplates any suitable technique for forming a mold of one or more of the user's teeth using one or more polycaprolactone polymers. Furthermore, upper arch 12 may be coupled to lower arch 14, a mask, or other apparatus in some suitable manner to form a device suitable for preventing trauma injuries or treating breathing problems such as sleep apnea.

Alternatively, as shown in FIG. 1b, upper arch 12, lower arch 14, or both upper arch 12 and lower arch 14 may themselves be formed from a deformable material suitable for dental uses, for example, a deformable material that includes one or more of the polycaprolactone polymers or other aliphatic polyesters discussed above. A suitable light cured material, another polymer, or any other suitable material may be used to replace or combine with one or more of the polycaprolactone polymers in forming the deformable material, depending on the application. Whether upper arch 12 and lower arch 14 are themselves formed using one or more polycaprolactone polymers or are formed so as to include a deformable material 20 that includes one or more polycaprolactone polymers, upper arch 12, lower arch 14, or both upper arch 12 and lower arch 14 may be relined using one or more polycaprolactone polymers to more optimally fit the user's teeth.

FIGS. 2a and 2b illustrate a method for relining a dental device 11 using one or more of the polycaprolactone polymers or other aliphatic polyesters discussed above in connection with FIGS. 1a and 1b. A suitable light cured material, another polymer, or any other suitable material may be used to replace or combine with one or more of the polycaprolactone polymers in relining dental device 11. Referring to FIG. 2a, one or more of the user's upper or lower teeth, represented generally by tooth 16, have been pressed or otherwise inserted into some suitable deformable material 21 to form a first mold 28 of tooth 16 that resembles the outward surface 17 of tooth 16. Although upper arch 12 is discussed as including first mold 28, the present invention contemplates device 11 having lower arch 14 instead of, or in addition to, upper arch 12.

Tooth 16 is shown in its natural state within the user's gum 24. Deformable material 21 has been allowed to cool and harden or otherwise take a more permanent shape. Due to the tendency of deformable material 21 to contract during cooling, the impression made by the user's teeth has expanded to form a first mold 28 that does not optimally fit the user's teeth. Alternatively, first mold 28 may have been improperly formed, such that first mold 28 does not optimally fit the user's teeth. First offset 30 indicates the amount by which first mold 28 is separated from outward surface 17 when tooth 16 is positioned within upper arch 12. The present invention further contemplates forming first mold 28 using the upper arch 12 illustrated in FIG. 1b or any other suitable mold of one or more of the user's teeth.

A deformable material 32 is introduced into the region between outward surface 17 and first mold 28 from any suitable source 40, for example, a hot glue gun. Deformable material 32 couples to first mold 28 and wholly or partially fills the region between first mold 28 and the outward surface 17 of tooth 16. As a result, first offset 30 is reduced or eliminated, yielding a relined dental device 11 that more optimally fits one or more of the user's teeth. Deformable material 32 may be introduced into upper arch 12 and may couple to or otherwise combine with first mold 28 while deformable material 32 is in a liquid, melted, or other deformable state.

In one embodiment, deformable material 32 includes one or more of the polycaprolactone polymers or other aliphatic polyesters discussed above. Deformable material 32 may also include one or more other polymers or any other suitable mixture, compound, composition, or material, depending on the application. The present invention contemplates using one or more polycaprolactone polymers or other aliphatic polyesters in any suitable dental or other application for which a hot glue gun is used or desirable. As discussed above, deformable material 32 may cool and harden or otherwise take a more permanent shape relatively slowly and display increased thermoplasticity during cooling, compared to materials such as Elvax. This may provide the user or clinical professional with additional time to properly conform deformable material 32 to the shape of the user's teeth.

In one embodiment, although deformable material 32 wholly or partially surrounds tooth 16 and couples to first mold 28 while deformable material 32 is in a liquid or melted state, the user experiences little or no discomfort when deformable material 32 is introduced. This is due to a variety of factors, taken separately or in combination. First, since deformable material 32 includes one or more polycaprolactone polymers, alone or together with one or more other suitable materials, deformable material 32 may transfer relatively little heat to tooth 16 and the tissues of the user's mouth. Second, since deformable material 32 is introduced in a relatively thin layer, the volume of material transferring heat to tooth 16 and the tissues of the user's mouth is relatively small. Therefore, the user's mouth may absorb the heat transferred from deformable material 32 with little or no discomfort. Third, the user's teeth and the tissues of the user's mouth are generally well-adapted to exposure to hot substances, for example, hot food and liquids. The present invention contemplates other factors that may also contribute to the user experiencing little or no discomfort when deformable material 32 is introduced into device 11.

As shown in FIG. 2b, deformable material 32 couples to first mold 28 and forms a second mold 36 of tooth 16. In one embodiment, deformable material 32 mixes, reacts, or otherwise combines with deformable material 21 to form second mold 36. A second offset 34 indicates the thickness of the space, if any, between second mold 36 and the outward surface 17 of tooth 16. Although deformable material 32 may have a tendency to contract as it cools, second offset 34 is smaller than first offset 30. As a result, second mold 36 conforms to the shape of tooth 16 more optimally than did first mold 28. This is due, at least in part, to the dimensional stability displayed by the polycaprolactone polymers as deformable material 32 cools, which reduces the contraction of deformable material 32 during the cooling process.

As indicated by the dashed lines 39, upper arch 12 or lower arch 14 may remain inserted in the user's mouth or may be removed from the user's mouth before, during, or after deformable material 32 cools or otherwise hardens to form second mold 36. Once second mold 36 is formed, upper arch 12 may be repeatedly removed and reinserted into the user's mouth as appropriate for the treatment or other use for which device 11 was constructed. Furthermore, upper arch 12 may be coupled to lower arch 14, a mask, or other apparatus in some suitable manner to form a device suitable for preventing trauma injuries or treating breathing problems such as sleep apnea. A relined dental device and method is claimed and described in copending application Ser. No. 08/621,133, which is herein incorporated by reference.

FIG. 3a illustrates a deformable material 50 that has been conformed to the shape of at least a portion of a user's face to form a mask 52. In one embodiment, deformable material 50 includes one or more of the polycaprolactone polymers discussed above, and may also include one or more other polycaprolactone or other polymers or any other suitable material. Deformable material 50 is placed in its deformable state and spread over at least a portion of the surface of the user's face so as to conform to the shape of the user's face over one or more contact regions. Straws or other breathing tubes may be inserted into the nostrils of the user beforehand, so that breathing channels 54 are formed in mask 52 when deformable material 50 cools or otherwise hardens to form mask 52. Because deformable material 50 includes one or more polycaprolactone polymers, deformable material 50 may cool relatively slowly, have increased thermoplasticity during cooling, and display increased dimensional stability during cooling, compared to materials such as Lexan or Elvax.

Mask 52 may be coupled to strap attachment 58 and strap 56 to allow the user to secure mask 52 about the user's head. A continuous positive air pressure (CPAP) device may be attached to mask 52 in some suitable manner, for example, using a deformable material that includes one or more polycaprolactone polymers or any other suitable material, to deliver a gas to the user's nose. Mask 52 may be coupled to any dental or other suitable device designed to prevent trauma injuries or treat breathing problems such as sleep apnea. The present invention contemplates using mask 52 in any suitable manner, whether or not mask 52 is coupled to a dental or other device.

Figure 3B:
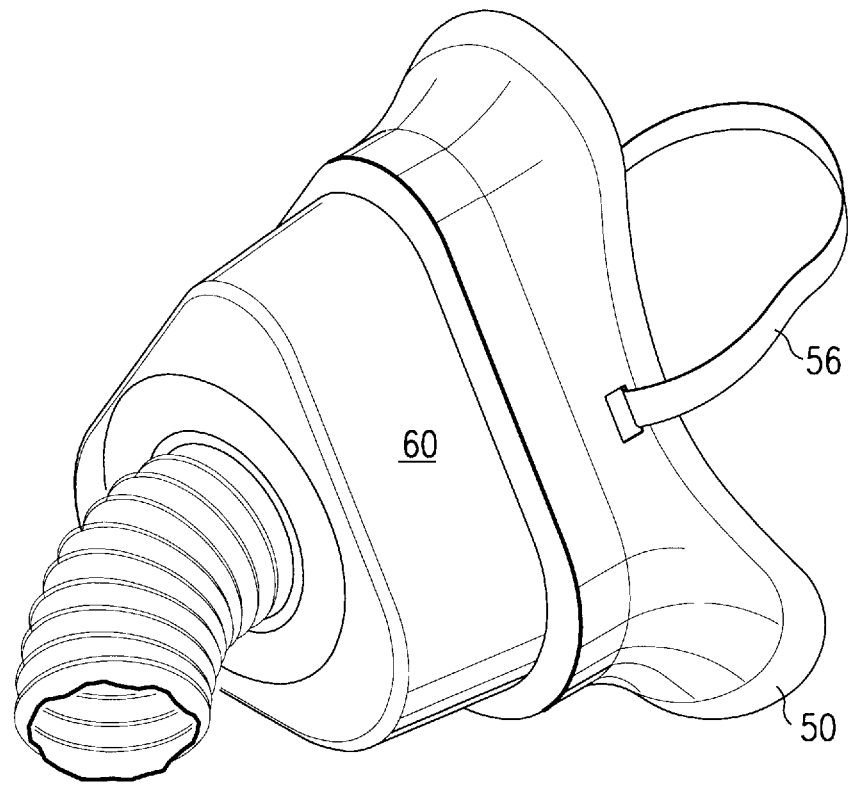

As shown in FIG. 3b, deformable material 50 may be used to customize an existing mask 60 for a particular user. Deformable material 50 is placed in a deformable state and coupled to mask 60 around at least a portion of the perimeter of mask 60 so as to conform to the shape of the user's face. In one embodiment, polyvinyl siloxane may replace or combine with deformable material 50 to customize mask 52 or mask 60 for a particular user. For example, polyvinyl siloxane may be formed around at least a portion of the perimeter of mask 52 or mask 60, as the case may be, so as to conform to the shape of the user's face. The polyvinyl siloxane may be coupled to deformable material 50 after deformable material 50 has been used to customize mask 60.

The present invention contemplates forming or customizing a mask in any suitable manner using one or more polycaprolactone polymers.

Although the present invention has been described above in connection with several embodiments, it should be understood that a plethora of changes, substitutions, variations, alterations, transformations, and modifications may be suggested to one skilled in the art, and it is intended that the present invention encompass such changes, substitutions, variations, alterations, transformations, and modifications as fall within the spirit and scope of the appended claims.

What is claimed is:

1. A dental device, comprising:
   an arch adapted to receive one or more of a user's teeth;
   a deformable material coupled to the arch, the deformable material comprising a first aliphatic polyester; and
   a mask coupled to the arch.

2. The device of claim 1, wherein the mask comprises the first aliphatic polyester.

3. A method for forming and inserting a dental device into a user's mouth, comprising the steps of:
   coupling a deformable material to an arch while the arch is in a user's mouth, the arch adapted to receive one or more of the user's teeth, the deformable material comprising a first aliphatic polyester;
   allowing the deformable material to form a mold of the user's teeth; and inserting the formed device, including the arch and the deformable material, into the user's mouth to perform a function selected from the group consisting of:
   preventing injury; and
   treating a breathing disorder.

4. The method of claim 3, wherein the first aliphatic polyester comprises a first polycaprolactone polymer.

5. The method of claim 3, wherein the first aliphatic polyester has the formula:

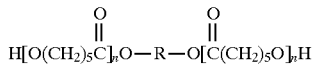

wherein R is an aliphatic hydrocarbon.

6. The method of claim 3, wherein the first aliphatic polyester comprises a homopolymer of caprolactone initiated with a diol.

7. The method of claim 3, further comprising the step of combining a second polymer with the first aliphatic polyester to form the deformable material.

8. The method of claim 3, further comprising the step of combining a second aliphatic polyester with the first aliphatic polyester to form the deformable material.

9. The method of claim 3, further comprising the step of forming a mold of one or more of the user's teeth using the deformable material.

10. The method of claim 9, wherein the mold is formed while the device is in the user's mouth.

11. The method of claim 3, wherein the arch comprises the first aliphatic polyester.

12. The method of claim 3, wherein the deformable material is coupled to the arch while the device is in the user's mouth.

13. The method of claim 3, wherein the deformable material is coupled to the arch while the deformable material is in a liquid state.

14. A method for forming a dental device for use in a user's mouth, comprising the steps of:
    coupling a deformable material to an arch, the arch adapted to receive one or more of the user's teeth, the deformable material comprising a first aliphatic polyester;
    coupling a mask to the arch; and
    wherein the use is selected from the group consisting of:
    preventing injury; and
    treating a breathing disorder.

15. A method for forming a dental device for repeated use in a user's mouth, comprising the steps of:
    forming a first mold of a tooth of the user; and
    coupling a deformable material to the first mold while the first mold is in the user's mouth, the deformable material operable to form a second mold of the tooth, the deformable material comprising a first aliphatic polyester, the device operable to be repeatedly used in the user's mouth, wherein the repeated use is selected from the group consisting of:
    preventing injury: and
    treating a breathing disorder.

16. The method of claim 15, wherein the first aliphatic polyester comprises a first polycaprolactone polymer.

17. The method of claim 15, wherein the first aliphatic polyester has the formula:

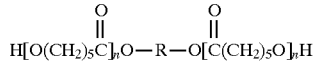

wherein R is an aliphatic hydrocarbon.

18. The method of claim 15, wherein the deformable material further comprises a second polymer.

19. The method of claim 15 wherein the deformable material further comprises a second aliphatic polyester.

20. The method of claim 15, wherein the deformable material is coupled to the first mold while the device is in the user's mouth.

21. The method of claim 15, wherein the deformable material is coupled to the first mold while the deformable material is in a liquid state.

22. The method of claim 15, wherein the deformable material forms the second mold of the tooth while the device is in the user's mouth.

* * * * *